US009638394B2

(12) United States Patent
Cai et al.

(10) Patent No.: US 9,638,394 B2
(45) Date of Patent: May 2, 2017

(54) LIGHT EMITTING DIODE (LED) LIGHTING SYSTEM WITH ANTIMICROBIAL/AIR CLEANING FUNCTIONS FROM HIGHLY SPECULAR MULTILAYER THIN FILM REFLECTOR

(71) Applicant: GE Lighting Solutions, LLC, East Cleveland, OH (US)

(72) Inventors: Dengke Cai, Willoughby, OH (US); Matthew A. Bugenske, East Cleveland, OH (US); Michael Vincent Yee, East Cleveland, OH (US); Cherian Jacob, East Cleveland, OH (US); Koushik Saha, Brunswick, OH (US); Mark Edward Kaminski, East Cleveland, OH (US); Benjamin James Ward, Beachwood, OH (US)

(73) Assignee: GE LIGHTING SOLUTIONS, LLC, East Cleveland, OH (US)

( * ) Notice: Subject to any disclaimer, the term of this patent is extended or adjusted under 35 U.S.C. 154(b) by 0 days.

(21) Appl. No.: 14/447,900

(22) Filed: Jul. 31, 2014

(65) Prior Publication Data
US 2016/0033110 A1    Feb. 4, 2016

(51) Int. Cl.
*F21V 7/22*    (2006.01)
*F21K 9/90*    (2016.01)
(Continued)

(52) U.S. Cl.
CPC    *F21V 7/22* (2013.01); *A61L 2/00* (2013.01); *A61L 9/00* (2013.01); *A61L 9/205* (2013.01);
(Continued)

(58) Field of Classification Search
CPC .................................................. F21V 7/22
(Continued)

(56) References Cited

U.S. PATENT DOCUMENTS 5,412,274 A * 5/1995 Parham ............... C03C 17/3417
                                                            313/112
6,013,372 A    1/2000 Hayakawa et al.
(Continued)

FOREIGN PATENT DOCUMENTS

JP    2005122955 A    5/2005
WO    2009056838    5/2009

OTHER PUBLICATIONS

Michael et al., "Silver Doped Titanium Dioxide Nanomaterials for Enhanced Visible Light Photocatalysis", Journal of Photochemistry and Photobiology A: Chemistry, vol. No. 189, Issue No. 2-3, pp. 258-263, Jun. 25, 2007.
(Continued)

*Primary Examiner* — Jacob R Stern
(74) *Attorney, Agent, or Firm* — GE Global Patent Operation; Peter T. DiMauro

(57) ABSTRACT

A system and method according to various embodiments can include a lighting fixture comprising a light source. A multilayer thin film coated reflector is applied to an outer light emitting surface of the lighting fixture. A top layer of the multilayer thin film coated reflector comprises a material including an anatase TiO crystal structure that exhibits antimicrobial properties when activated by the light source.

11 Claims, 5 Drawing Sheets

(51) Int. Cl.
  *A61L 9/20* (2006.01)
  *F21V 33/00* (2006.01)
  *A61L 2/00* (2006.01)
  *A61L 9/00* (2006.01)
  *F21K 9/233* (2016.01)
  *F21K 9/60* (2016.01)
  *C08K 3/22* (2006.01)
  *F21Y 115/10* (2016.01)

(52) U.S. Cl.
  CPC ............ *F21K 9/233* (2016.08); *F21K 9/60* (2016.08); *F21K 9/90* (2013.01); *F21V 33/0064* (2013.01); *C08K 2003/2241* (2013.01); *F21Y 2115/10* (2016.08)

(58) Field of Classification Search
  IPC .......... A61L 2/00, 9/00, 9/205; C08K 2003/22; F21K 9/137, 9/50, 9/90; F21V 33/0064, 7/22; F21Y 2101/02
  See application file for complete search history.

(56) References Cited

U.S. PATENT DOCUMENTS

| | | | |
|---|---|---|---|
| 6,154,311 A * | 11/2000 | Simmons, Jr. | G02B 5/208 359/350 |
| 6,764,655 B1 | 7/2004 | Nishii et al. | |
| 2002/0084749 A1 * | 7/2002 | Ayala | H01L 33/44 313/512 |
| 2006/0007677 A1 * | 1/2006 | Israel | G02B 5/0808 362/227 |
| 2006/0086252 A1 | 4/2006 | Huang | |
| 2007/0230181 A1 | 10/2007 | Fujishima et al. | |
| 2009/0041632 A1 | 2/2009 | Day et al. | |
| 2014/0004334 A1 * | 1/2014 | Kalyankar | G02B 1/115 428/312.6 |

OTHER PUBLICATIONS

Giulio et al., "Photo-Catalytic Coating of Polystyrene for Household Cooling Appliances with Self Cleaning Surfaces", Journal of Applied Electrochemistry, vol. No. 39, Issue No. 11, pp. 2265-2273, 2009.

Zhou et al., "Ag2O/TiO2 Nanobelts Heterostructure with Enhanced Ultraviolet and Visible Photocatalytic Activity", ACS Applied Materials & Interfaces, vol. No. 2, Issue No. 8, pp. 2385-2392, Aug. 2010.

Winzenburg et al., "Efficient Photocatalysis in the Visible with TiO2/Phthalocyanine-Hybrid Particles", 3rd International Symposium on Ultra-High Performance Concrete and Nanotechnology for High Performance Construction Materials, At Kassel, vol. No. 3, pp. 177-184, Mar. 2012.

PCT Search Report and Written Opinion issued in connection with corresponding Application No. PCT/US2015/037883 on Sep. 18, 2015.

* cited by examiner

LIGHT EMITTING DIODE (LED) LIGHTING SYSTEM WITH ANTIMICROBIAL/AIR CLEANING FUNCTIONS FROM HIGHLY SPECULAR MULTILAYER THIN FILM REFLECTOR

I. FIELD OF THE INVENTION

The present disclosure relates generally to light emitting diode (LED) reflectors. More particularly, the present disclosure relates to a reflector apparatus coated with a thin film comprising antimicrobial cleaning properties.

II. BACKGROUND OF THE INVENTION

A cleanroom is a controlled environment in which the concentration of airborne particles is controlled to specified limits. Airborne contamination must be continually removed from the air. The level to which these particles need to be removed depends upon the regulatory standards required. Whole room decontamination may be performed periodically or continuously to remove or neutralize contaminants from indoor environments to ensure that a desired decontamination level is achieved.

Clean room environments and whole room decontamination are of immense value in many industries, including healthcare, aerospace, medical device production, semiconductors, and pharmaceutical. The low density of environmental pollutants such as airborne microbes, bacteria, particles, and dust within these facilities reduces the amount of contamination within these facilities.

The only way to control contamination is to control the total environment. Eliminating airborne contamination is really a process of control. These contaminants are generated by people, process, facilities and equipment. For example, in the healthcare industry, it is estimated that between 5% and 10% of patients admitted to hospitals acquire one or more healthcare-associated infections, which leads to more than a million people worldwide being affected by infections acquired in hospitals. Health-care associated infections are also an important problem in extended care facilities, including nursing homes and rehabilitations units. These health-care acquired infections are associated with nearly 100,000 deaths annularly.

Patients infected with healthcare-associated microbes frequently contaminate items in their immediate vicinity with microbes that may remain viable on surfaces for days to weeks. Contaminated surfaces in healthcare facilities contribute to the spread of healthcare-associated microbes. In some instances, patients acquire microbes following direct contact with contaminated equipment or other surfaces. Contaminated surfaces can act as sources from which healthcare workers contaminate their hands. Healthcare workers can contaminate their hands by touching contaminated surfaces, and can transmit microbes if their hands are not cleansed appropriately.

Another critical source of contamination is inadequate cleaning of rooms after discharging a patient with certain contagious diseases, which puts subsequent patients admitted to the room at risk of acquiring the organism. Routine cleaning of patient rooms is often below the required standard. Therefore, improved cleaning and disinfection of the environment can reduce the risk of patients acquiring multi-drug resistant microbes. Cleaning, disinfecting and sterilization save lives and improve patient outcomes. Providing patients with a safe environment of care requires appropriate cleaning and disinfection of medical equipment and environmental surfaces.

Accordingly, much research has been devoted toward preventing growth of bacteria by the use of antimicrobial agents. Conventional techniques employed in the lighting industry to reduce bacterial growth and maintain a sanitary environment include, for example, using anatase type titanium dioxide ($TiO_2$) or metal doped anatase type $TiO_2$ like Zn, Si and Fe etc., as photocatalysts. This process exposes ultraviolet light to a catalyst such as titanium dioxide to produce primarily hydroxyl radicals (OH). These hydroxyl radicals are extremely reactive and can oxidize or "break down" pathogens and pollutants such that it can be used in indoor environments for air disinfection, as well as for contact-surface and materials disinfection. This process can be used to reduce indoor pathogens and pollutants to the extent that an acceptable indoor air quality can be achieved.

Therefore, antimicrobial agents comprising anatase $TiO_2$ have been found to be useful blended with materials such as plastics, paintings and coatings, which also have applications in facilities such as hospitals. Oftentimes, these $TiO_2$ antimicrobial agents have been applied as a coating within a lighting fixture installed in such facilities to disinfect the air and to clean surfaces contaminated with disease pathogens.

In addition, reflectors have also been an essential component of lighting applications for many years. In various types of reflectors, the reflective surfaces are coated with multilayer thin films. Such multilayer thin films typically incorporate a large number of thin layers of different light transmissive materials. The layers are often referred to as micro-layers, because they are thin enough so that the reflection and transmission characteristics of the film are determined in large part by constructive and destructive interference of light reflected from the layer interfaces.

Some reflective films are designed to reflect specularly. Such reflective surfaces can be formed from or coated with a highly specular material. Thus, the specular design of the highly specular surfaces can be a reflective base material or an applied highly specular coating.

The concept of specular reflection relates to the mirror-like reflection of light (or of other kinds of wave) from a surface, in which light from a single incoming direction (a ray) is reflected into a single outgoing direction. A pure specular reflector performs according to the law of reflection, which states "the angle of reflection equals the angle of incidence."

One benefit of highly specular surfaces is the ability to maintain a uniform light intensity distribution, which is critically important in a LED lighting application.

III. SUMMARY OF THE EMBODIMENTS OF THE INVENTION

Given the aforementioned deficiencies, a need exists for a lighting system and method that provides the combined benefits of improved reflectivity with air cleaning functions. A continuing need exists for a reflective coating having a highly specular reflectance and antimicrobial capabilities for use, especially, in a lamp or other lighting devices. There also remains a need for an improved efficiency LED light fixture with a reflector having 82% to 99% reflectance and air cleaning function.

There also remains a need to provide antimicrobial/antifungal to control microbial growth over the entire illuminating surface area of a lighting fixture. There remains a further need for a lighting system and method that provides clean room capability and/or whole room decontamination. There remains a further need for a clean room and controlled environment facility having the ability to control bacterial growth through the use of a ceiling light, which delivers a pleasant, uniform light to illuminate a room.

Under certain circumstances, an embodiment of the present invention includes a lighting fixture comprising a light source that emits light at wavelengths below 400 nm. A multilayer thin film coated reflector is applied to an outer light emitting surface of the lighting fixture. A top layer of the multilayer thin film coated reflector comprises anatase titanium dioxide ($TiO_2$) that exhibits antimicrobial properties at wavelengths below 400 nm when activated by the light source.

A method of using a lighting system according to various exemplary embodiments can include adding a multilayer thin film coating to an outer light emitting surface of a lighting fixture comprising a light source that emits light at a wavelength below 400 nm; and applying a top layer to multilayer thin film coated reflector, wherein the top layer comprises titanium dioxide ($TiO_2$) that exhibits antimicrobial properties when activated by the light source that is emitting at wavelengths below 400 nm.

Further features and advantages, as well as the structure and operation of various embodiments, are described in detail below with reference to the accompanying drawings. The invention is not limited to the specific embodiments described herein. The embodiments are presented for illustrative purposes only. Additional embodiments will be apparent to persons skilled in the relevant art(s) based on the teachings contained herein.

IV. BRIEF DESCRIPTION OF THE DRAWINGS

Figure 1:
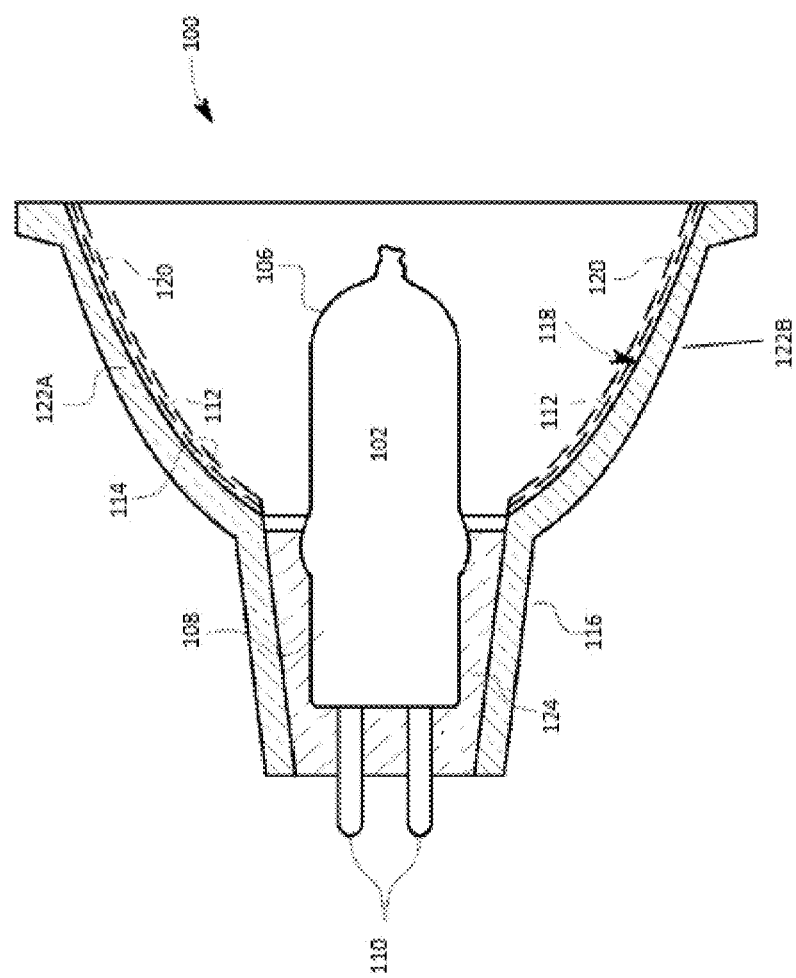
FIG. 1 is an illustration of a cross-sectional view of an exemplary lighting system that includes a reflective coating in accordance with the present teachings.

The present disclosure may take form in various components and arrangements of components, and in various process operations and arrangements of process operations. The present disclosure is illustrated in the accompanying drawings, throughout which, like reference numerals may indicate corresponding or similar parts in the various figures. The drawings are only for purposes of illustrating preferred embodiments and are not to be construed as limiting the disclosure. Given the following enabling description of the drawings, the novel aspects of the present disclosure should become evident to a person of ordinary skill in the art.

V. DETAILED DESCRIPTION OF VARIOUS EMBODIMENTS

The following detailed description is merely exemplary in nature and is not intended to limit the applications and uses disclosed herein. Further, there is no intention to be bound by any theory presented in the preceding background or summary or the following detailed description.

Throughout the application, description of various embodiments may use "comprising" language, however, it will be understood by one of skill in the art, that in some specific instances, an embodiment can alternatively be described using the language "consisting essentially of" or "consisting of."

For purposes of better understanding the present teachings and in no way limit the scope of the teachings, it will be clear to one of skill in the art that the use of the singular includes the plural unless specifically stated otherwise. Therefore, the terms "a," "an" and "at least one" are used interchangeably in this application.

Unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. In some instances, "about" can be understood to mean a given value ±5%. Therefore, for example, about 100 nm, could mean 95-105 nm. At the very least, each numerical parameter should at least be construed in light of the number of reported significant digits and by applying ordinary rounding techniques.

Various embodiments provide a system and method that relates to a combination of technologies, including multilayer thin film coating technology, UV brightener technology, and LED indoor downlight technology. In various embodiments, the system and method provides an LED downlight module containing a 99% reflectivity specular thin film reflector, which exhibits air cleaning properties.

In various embodiments, a LED lighting system is provided by depositing a multilayer thin film coating reflector on a metal, glass, or ceramic substrate. In various embodiments, the thin film reflector is based on a multilayer dielectric layer consisting predominantly of $SiO_2$ and $TiO_2$ and provides 99% specular reflectivity.

In various embodiments, the outer layer of the thin film coated reflector is $TiO_2$. In various embodiment, the top layer of the thin film coating is $TiO_2$ including anatase crystal. By subjecting the $TiO_2$ to rapid thermal annealing (RTA), amorphous $TiO_2$ can transit to anatase type $TiO_2$, which provides air cleaning function under 400 nm wavelength. The coating comprises substances capable of absorbing light waves within the UV spectrum (i.e., light waves having a wavelength ranging from about 100 nanometers (nm) to about 400 nm). Thus, in various embodiments, the lighting system includes a light emitting diode that emits a wavelength below 400.

In various embodiments, a system and method is provided that exposes ultraviolet and blue light to a catalyst such as anatase titanium dioxide ($TiO_2$), as a photocatalyst. The system and method combines the photocatalyst effect with the physical inhibitions of a micro-pattern surface to provide antimicrobial properties for disinfection and contaminant degradation.

Various embodiments provide a coating with over 90% reflectance at a nominal incident angle.

In various embodiments the system and method provides a multilayer $TiO_2$ and $SiO_2$ coating deposited on a porcelain coated metal substrate with 99% reflectance. By performing an additional annealing process, anatase crystal $TiO_2$ is increased to enable antimicrobial capabilities.

FIG. 1 shows one particularly suitable use of a reflective coating 120 prepared according to the present teachings and applied on a lighting fixture 100. The lighting fixture 100 can include a light source, such as an LED luminaire 102. In general, the luminaire 102 is a complete lighting unit consisting of a single or multiple lamps together with the parts designed to distribute the light, to position and protect the lamps, and to connect and interface the lamps to the power source. The details of the components of the luminaire will not be described herein, because it is not the subject of the invention.

As shown, the lighting fixture 100 includes a lamp and reflector combination, which comprises lamp 102 having a vitreous envelope 106 hermetically sealed at 34 by means of a customary pinch and seal or shrink seal and having exterior leads 110. Lamp 102 is cemented into the cavity of the substrate 122 (e.g. a glass reflector) by cement 124 using suitable cements for securing the lamp in the reflector, which are generally known in the art. Lamp 102 may also contain a filament and in-leads or an arc (not shown) within envelope 106. Alternatively, lamp 102 may be a solid state light source that comprises, e.g., one or more light emitting diodes.

In various embodiments, the lamp 102 may be an LED-based lamp configured as an indoor downlight in which LEDs are mounted on a substrate in an arrangement that provides illumination in a generally downward direction. The LED downlight fixture 102 may comprise an LED array formed of a plurality of LEDs and may include suitably configured reflectors. In various embodiments, the LED includes a reflector assembly with a diffuser (not shown) positioned therein. The LED and diffuser positioned within the reflector assembly provide ample light cut-off, reduced glare and increased light efficiency.

As shown in FIG. 1, the reflective coating 120 is applied on the interior surface 114 of the parabolic portion 118 of the substrate 122, which may be a glass substrate, a metal substrate, etc. However, in other embodiments, the reflective coating 120 can be disposed on the outer surface 116 of the substrate 122. The reflective coating 120 may be positioned directly on the inner surface 114, or onto an optional primer coating 112, if desired. For example, the primer coating 112 can improve adherence and/or reflectance of the reflective coating 120.

During operation of the lamp and reflector combination 100, little or none of the light emitted by the lamp 102 is discernible from the outside surface 116 of the substrate 122, due to the reflective coating 120 present on the substrate 122.

Figure 2:
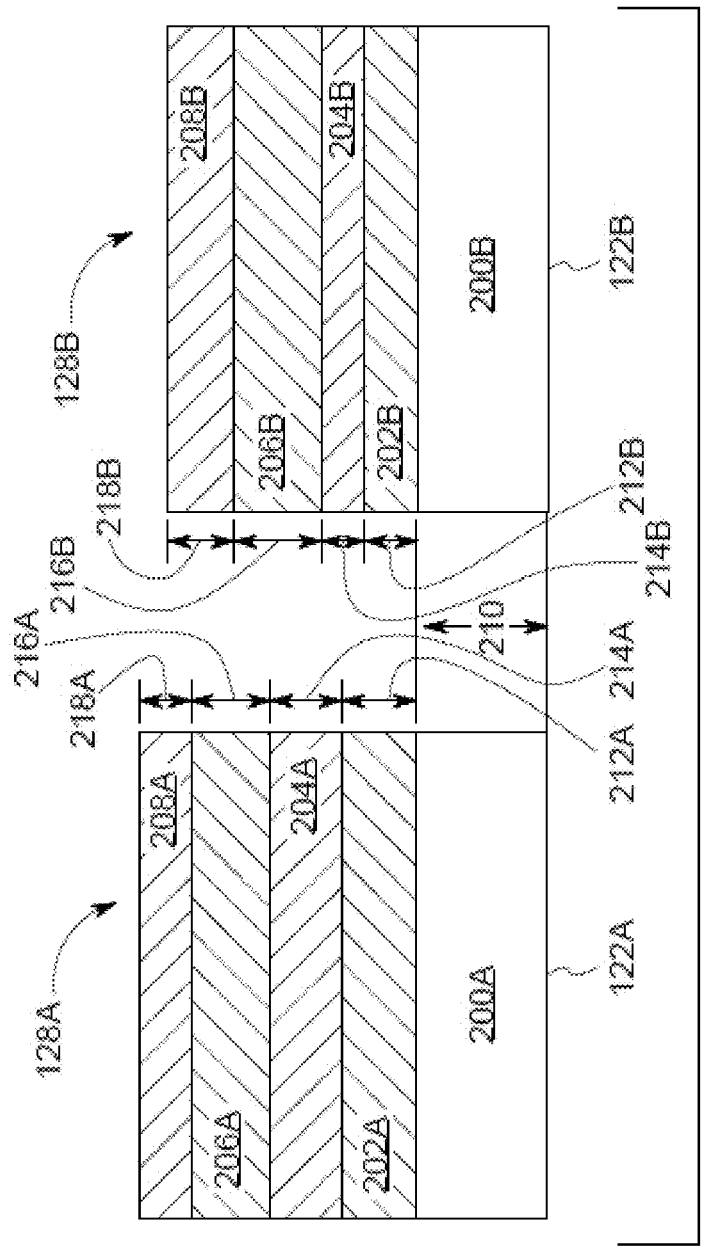
FIG. 2 illustrates a partial cross-sectional view of a multi-reflector system including multilayer reflectors in accordance with the present teachings.

FIG. 2 shows exemplary reflectors that can utilize the reflective coating formed according to the presently described methods. FIG. 2 shows partial cross sections of the two example reflectors 122A, 122B of a lighting system. In the example shown in FIG. 2, the lighting system illustrated can be referred to as a multi-reflector system, having multiple reflectors 122A, 122B. While two reflectors 122A, 122B are shown, the lighting system in various embodiments includes any number of distinct reflectors, and any of the reflectors may or may not be connected directly to each other.

The system in other embodiments (as shown in FIG. 1) can include a single reflector component 122, e.g., an asymmetrical reflector. However, and while multiple reflectors 122A, 122B are shown schematically as separate components, two or more of the reflectors 122A, 122B are in some embodiments connected to each other, e.g., directly. The combined reflector of such embodiments, including, e.g., each illustrated reflector component 122A, 122B of FIG. 2, may share a common substrate or have connecting substrates, for instance.

Each reflector 122A, 122B includes a substrate, or base reflector surface 200A, 200B. The base reflector surfaces 200A, 200B may include any of a variety of materials. In various embodiments, the substrate comprises a metal substrate. In one embodiment, one or both base surfaces 200A, 200B are non-reflective or minimally reflective. In one embodiment, one or both base surfaces 200A, 200B are reflective. As an example of the latter case, one or both base surfaces 200A, 200B can include aluminum or silver. In the preferred embodiment, the substrate is formed of aluminum.

As shown in FIG. 2, each thin-film reflective stack 128A, 128B includes multiple layers positioned directly adjacent (i.e., directly atop, in the view of FIG. 2) the reflector base 200A, 200B. The stacks 128A, 128B in these embodiments include multiple relatively thin stacked layers or films of, e.g., dielectric material.

Various characteristics or factors define each stack 128A, 128B. Characteristics include a number, size (e.g., thickness), and material of stack layers. One or more of the characteristics are, according to the present technology, a function of lighting system geometry and optics.

The system geometry factors can include a configuration (e.g., size and shape) and arrangement (e.g., positioning and orientation) of the reflectors 122A, 122B in the system.

The optical factors can include at least those resulting from the system geometry, such as the incident angles of light on the light stack 128A, 128B. The optical factors can also include color presence or distribution (e.g., wavelength range, or median wavelength, etc.) of the light to arrive at the stacks.

While each stack 128A, 128B is shown to include four layers each, for illustrative purposes, the stacks can include any desired number of layers. The number of layers can be even or odd. The number in some embodiments, is greater than four—e.g., five layers, ten layers, fifteen layers, twenty layers, numbers between these, or greater than these. In a preferred embodiment, at least one of stack 128A, 128B includes twenty-six (26) layers.

The layers can include any of a variety of materials. In some embodiments, each layer consists preferably of a dielectric material. In some embodiments, each stack 128A, 128B includes at least two different material layers, such as two different dielectric materials. The layers can vary by their characteristic of refractive index. In a contemplated embodiment, at least one of the layers is a non-dielectric.

In one embodiment, the layers of each stack 128A, 128B include alternating layers of a first material (e.g., first dielectric material) having a relatively high refractive index and a second material (e.g., second dielectric material) having a relatively low refractive index. In this alternating arrangement, each relatively high refractive index material can be the same, and each relatively low refractive index material can be the exact same, but that need not be the case in every implementation.

For some implementations, it is preferred that the number of layers be even (e.g. 26 layers). In other embodiments, the number of layers may be odd. In at least one of those implementations, it is preferred that the final layer (e.g., top layer) also include a relatively high refractive index film.

The refractive index (n) of a material is the ratio of the speed of light in vacuum (c) and the speed of light within the material (v), or $n=c/v$. While the materials used in an dielectric stack may have other refractive indexes, in one of the embodiments having an alternating high-index/low-index arrangement, relatively high refractive indexes are between about n=2.2 and about n=2.6 nm—e.g., about n=2.4, and relatively low refractive indexes are between about n=1.2 and about n=1.8—e.g., about n=1.5.

Continuing with the example of FIG. 2, the stacks 128A, 128B begin with a low, or least relatively low, refractive index layer 202A, 202B positioned directly adjacent, and contacting directly, the substrates 200A, 200B, respectively. According to the alternating arrangement, the next layers 204A, 204B thus have a high, or relatively high, refractive index.

The final two layers illustrated are, then, continuing with the alternating arrangement, low refractive index layers 206A, B and high refractive index layers 208A, B.

The layers 202A/B, 204A/B, 206A/B, 128A/B of the stacks 128A, 128B can also be set to any of a wide variety of thicknesses. In FIG. 2, a thickness of the substrate 200A, 200B is identified by reference numeral 210. Thicknesses of the layers 202A/B, 204A/B, 206A/B, 128A/B are referenced by numerals 212A/B, 214A/B, 216A/B, and 218A/B, respectively.

Layer thicknesses for each implementation can be represented by, e.g., a linear measure, such as nanometers (nm) or millimeters (mm). In one embodiment, each layer 202A/B, 204A/B, 206A/B, 128A/B of the stacks 128A, 128B has a thickness of between about 15 nm and about 300 nm. The substrate, or base surface 200A, 200B, and any superstrate are in some cases much thicker. In one embodiment, for example, the substrate has a thickness approximately 5 mm. Any superstrate can be of similar thickness.

More particularly, the thickness for one or more of the layers of each reflector component can be pre-selected based on an expected angle or angles (or angle range) of incidence at which light from the source (such as lamp 102 in FIG. 1) will impinge on the stack 128A, 128B.

As discussed above, reflective coatings are used to selectively reflect or transmit light radiation from various portions of the electromagnetic radiation spectrum, such as ultraviolet, visible, and/or infrared radiation. For instance, reflective coatings are commonly used in the lamp industry to coat reflectors and lamp envelopes to improve the illumination efficiency or efficacy. According to the present teachings, the coating comprises substances capable of absorbing light waves within the UV spectrum (i.e., light waves having a wavelength ranging from about 100 nanometers (nm) to about 400 nm). Thus, in various embodiments, the lighting system includes a light emitting diode that emits light at wavelengths below 400.

In addition to the reflectance (R %) of the reflective coating applied to the reflectors, the coating can also be described in terms of angular distribution of reflectance, known as the bi-directional reflectance distribution function (BRDF) In general, BRDFs may be characterized as specular (mirror-like) and diffuse. A perfectly specular reflector obeys Snell's Law whereby all light rays exit from the surface at a reflection angle, θ, relative to the normal that is same as the incident angle, θ, if the surface is embedded in air, having index of refraction=1. A perfectly diffuse reflector has a Lambertian BRDF whereby the distribution of reflected light varies as cos(θ), independent of the incident angle. Practical reflectors are neither perfectly specular, nor perfectly diffuse. Any practical specular reflector will have a small component of diffuse reflectance, generally known as scatter or haze. Any practical diffuse reflector will have a small specular component of reflection. A diffuse reflector having a relatively high specular component is generally known as glossy, while a reflector having near zero specular component is generally known as matte or flat. In specular reflection, the angle of the light reflected from the surface is equal and opposite to the angle of the incident light.

Reflectors designed according to the present teachings are intended to use each part of the reflector surface to intercept an amount of radiant energy from a light source and reflect it directly to the area to be illuminated. This challenge is more easily met if the majority of the reflections are specular.

Therefore, a thin-film coated multilayer reflector having high reflectivity and high specularity is preferred according to the present teachings. In preferred embodiments, the thin film reflector is based on a multilayer dielectric layer consisting predominantly of $SiO_2$ and $TiO_2$ and provides 99% specular reflectivity. In preferred embodiments, the outer layer 120, 208A, 208B of the thin film coating is $TiO_2$, which includes anatase crystal prepared according to the process described below.

Thus, the reflective coating provides a light-emitting article having a reflectivity high enough to enhance the efficiency of the illumination system. The coating has over a 90% reflectance at a nominal incident angle. The coating has a total reflectivity of at least about 90 percent, preferably at least about 93 percent, more preferably at least about 94 percent and most preferably at least about 95 percent. For example, the reflective coating can reflect at least about 90% light in the UV spectrum at a 75° incident angle.

Applying a coating to the surface of reflector can be accomplished, for example, in a facile manner employing a low pressure vapor deposition coating (LPCVD) coating process for applying alternating layers of high and low refractive index materials. In a representative LPCVD process, a suitable metal organic precursor is introduced into a decomposition chamber wherein it is decomposed or reacted to form the metal oxide on a heated substrate. Separate layers of, for example, silica ($SiO_2$) and tantala or titania (titanium dioxide ($TiO_2$)) are applied onto the substrate. Such chemical vapor deposition techniques are well known to those skilled in the art. In forming the alternating layers of titania (or tantala) and silica on a glass reflector in accordance with an exemplary embodiment of the present teachings, the reflector is positioned within a deposition chamber, which is generally contained within a furnace. For an LPCVD process, the desired metal organic precursor, such as titanium ethoxide or tetraethylorthosilicate, in the vapor state is permitted to flow into the deposition chamber. It is decomposed to deposit a film of either titania or silica on the substrate. Individual layers of titania and silica can be uniformly deposited employing this process and have been successfully deposited on both flat and curved substrates such as lamp envelopes. In various embodiments, one or more layers may be disposed on the substrate so as to define a pattern. This is merely an example of a process of preparing the coating. Other known processes or proprietary processes can be utilized to produce the coating on the reflector.

In a demonstrated example, a multilayer $TiO_2$ and $SiO_2$ coating deposited on a porcelain coated metal substrate with 99% reflectance was prepared. The multilayer reflector included twenty-six (26) layers. The outer layer of the thin film coated reflector consisted of $TiO_2$. After the application of the coating onto the substrate, an annealing process was performed so that anatase crystal $TiO_2$ is increased to enable antimicrobial capabilities.

In various embodiments, the outer layer of the thin film coating is $TiO_2$ including anatase crystal. The coating comprises substances capable of reflecting light waves within the UV spectrum (i.e., light waves having a wavelength ranging from about 100 nanometers (nm) to about 400 nm). By subjecting the $TiO_2$ to rapid thermal annealing (RTA), amorphous $TiO_2$ can transit to anatase type $TiO_2$, which provides air cleaning function when activated by the light source that is emitting in a range that includes sub-400 nm wavelengths. Thus, in various embodiments, the lighting system includes a light emitting diode that emits a wavelength below 400.

As an antimicrobial agent, titanium dioxide (TiO2) has been widely used as a photocatalyst for disinfection and contaminant degradation. In order to be used as a photocatalyst, titanium has to exhibit anatase type crystallinity. Thus, in a case where amorphous titanium is formed from a titanium-based starting material through hydrolysis and condensation polymerization, there is a necessity to carry out a heat treatment to convert the amorphous titanium dioxide to an anatase type titanium dioxide.

Titanium dioxide can exist in amorphous form in three crystalline phases of brookite, anatase and rutile. Rutile titanium dioxide is the most common form, while anatase is the rarest form of titanium dioxide. Choosing the appropriate annealing temperature allows the structure to be made up of the defined portions of anatase and/or rutile. Anatase is a type of polymorph, which becomes a rutile when it is exposed to about 915° C.

According to the present teaching, after that application of the final (outer) layer of $TiO_2$, a multilayer $SiO_x/TiO_x$ reflector, preferably comprising 26 layers, is produced. Then, a rapid thermal annealing (RTA) process is performed to induce in the top (outer) layer of $TiO_2$ a transition from amorphous to anatase phase $TiO_2$ in an oxygen deficient $TiO_2$-channel at a temperature of approximately 500° C. During the RTA process, the atmosphere of the heating furnace is controlled by controlling the amount of oxygen, annealing temperature and time. The annealing process may employ a single temperature, or various ramp and soak cycles can be employed. Due to the fact that aluminum (Al) is used as the substrate in the described exemplary embodiment, $TiO_2$ crystallization induced nucleation on glass substrate is avoided.

Figure 3:
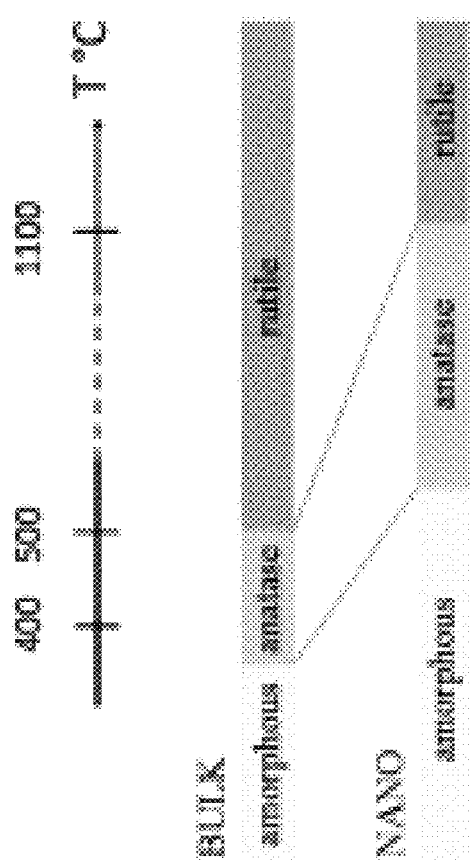
FIG. 3 is a characteristic diagram demonstrating a process to induce transition from amorphous titanium dioxide to anatase titanium dioxide in accordance with the present teachings.

As shown in FIG. 3 according to the present teachings, titanium dioxide having an anatase crystal structure can be formed at temperatures approximately 400° C.-500° C. to be useful for photocatalysis with response to ultraviolet photons.

In order for titanium dioxide to function as a photocatalyst, $TiO_2$ has to be activated by ultraviolet radiation. When a titanium dioxide surface is irradiated by UV light, the photocatalytic effect and hydrophilicity are activated together. This process creates hydroxyl radicals and superoxide ions, which are highly reactive electrons. These highly reactive electrons aggressively combine with other elements in the air, such as bacteria or pathogens, or contact surface and will kill these elements. Thus, $TiO_2$ is effective at performing self-cleaning to simultaneously disinfect both contaminated surfaces and airborne pathogens, effectively killing a broad spectrum of bacteria, viruses, molds and yeasts, including *Staphylococcus aureus, Escherichia coli* (*E coli*), *Klebsiella pneumonia*, MRSA *Straphylococcus aureus*.

As shown in FIG. 1, the reflective coating 120 may include several stacked layers (as shown in FIG. 2) comprising an antimicrobial film and a substrate. The antimicrobial film of $TiO_2$ functions as an outer film, which is positioned on the front side between the lighting fixture and the illuminated area. With the antimicrobial film on the front side of the lighting fixture exposed to the air, the antimicrobial film provides antimicrobial/antifungal properties released through surface coated antimicrobial compounds. Namely, the front side antimicrobial film provides antimicrobial/antifungal properties derived through top coatings antimicrobial/antifungal compounds within the film.

According to the present disclosure, the antimicrobial function is activated by a UV light source. Thus, an ultraviolet light-activated $TiO_2$ top (outer) layer is provided. According to various embodiments, UV and blue lights are utilized to activate anatase $TiO_x$ to derive a photocatalysis effect, which is also combined with the physical inhibition of the micro-pattern surface of the coating to produce an antimicrobial function on a lighting component and fixture.

It should be understood that the term "antimicrobial additive" as used throughout the disclosure means any chemical additive that reduces the level of bacteria, molds, fungi and other microbes and are commonly practiced as additives supplied directly into plastic materials, coatings, paints, etc. In various embodiments, one or more suitable antimicrobial additives can be selected from the following group: titanium dioxide, Ag, zinc and copper etc., and ions doped carriers such as zeolite, glass and some types of organic hosts, silver nano particles, tricolsan, and quartenary ammonium component, etc. This list is merely exemplary and is not exclusive.

An "antimicrobial coating", as used herein, refers to any coating or paint or surface grown layer that has antimicrobial function that can be applied to the surface of a device or component. Antimicrobial properties can be derived from the above mentioned antimicrobial additives blended within or applied as a coating itself, like TiO2, etc.

An "antimicrobial agent", as used herein, refers to a chemical that is capable of decreasing or eliminating or inhibiting the growth of microbes such a known in the art. The antimicrobial agent can be antimicrobial additive blended chemicals, an antimicrobial additive used alone, or any precursors that initiates an antimicrobial function after further reactions and processes, like crosslinking, crystalizing and polymerization etc.

In various embodiments, additives may be added to one or more layers of the reflector. Such layers may contain an optical brightener. An optical brightener is substantially colorless, fluorescent, organic compound that absorbs ultraviolet light and emits it as visible blue light. Only that fraction of the brightener which lies relatively near the surface will be exposed to sufficient ultraviolet light to activate the fluorescence of the brightener.

Brightener additives can be added to the material of the reflector without adversely affecting the reflectivity. Actually, optical brighteners can be used in order to improve the reflectivity. Optical brighteners can also be used to balance and fine-tune the reflectivity of the material.

In various embodiments, the reflecting material, and brightener can be combined at a predetermined ratio in advance before the reflective layer is coated on the substrate. The combination ratio of the reflecting material and the brightener can change depending on a desired specification.

Figure 4:
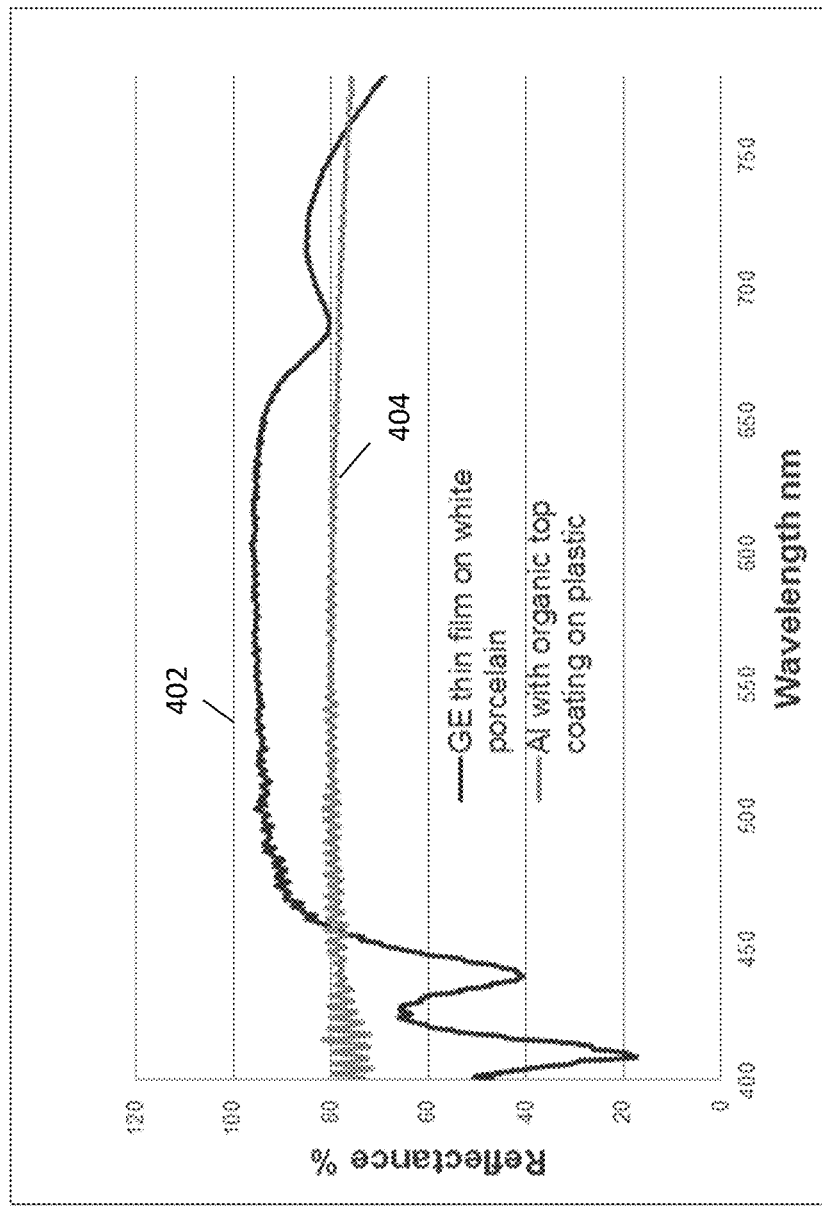
FIG. 4 is a chart showing a comparison of reflectance vs. wavelength of two reflective coatings.

Thus, the present disclosures most generally concerns an LED lighting apparatus with reflectors designed for improved efficiency in illuminating a desired area. According to various embodiments, provided is an LED lighting module with not only improved efficiency (comprising a reflector from 82% reflectance to 99%), but also exhibit air cleaning properties. To illustrate this point, FIG. 4 is a chart showing a comparison of the reflectance versus wavelength for two different reflectors 402, 404. Reflector 402 is a thin film deposited on a white porcelain coated steel reflector, which is prepared according to the present teaching. Reflector 402 exhibits 97% reflectance. In comparison, reflector 404 is a conventional aluminum reflector, which exhibits 80% reflectance.

Figure 5:
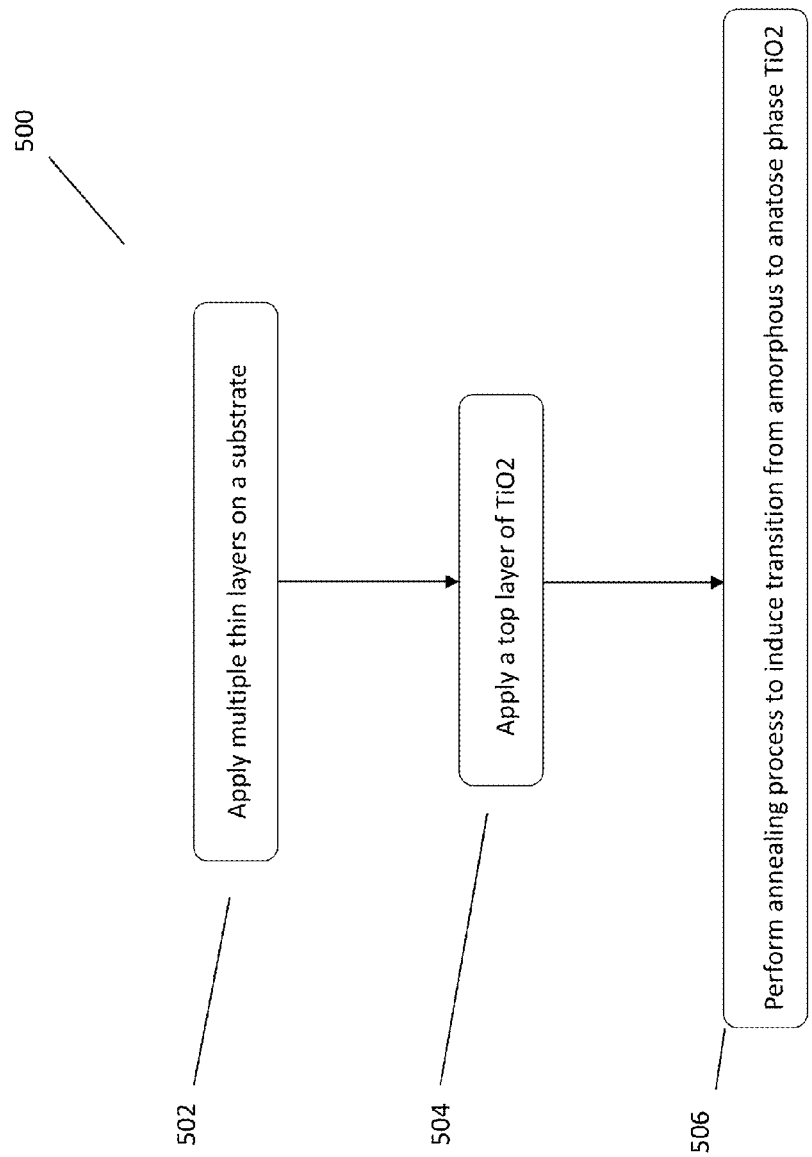
FIG. 5 is a flowchart of an exemplary method of practicing the present invention in accordance with the present teachings.

FIG. 5 is a flowchart explaining a method 500 for manufacturing a multilayer thin layer reflector according to the present teachings. In Step 502, multiple thin layers, comprising predominantly $SiO_x/TiO_x$, are applied on the front side of a substrate. In Step 504, a top (outer) layer comprising $TiO_2$ is applied. In Step 506, an annealing process is performed to induce in the top layer a transition from amorphous $TiO_2$ to anatase crystal $TiO_2$.

In general, the present teaching relates to a system and method that provide a lighting fixture exhibiting antimicrobial/antifungal capabilities over the entire light emitting area exposed to the air. In use, when the light fixture is activated the light contacts the antimicrobial compound causing the release of antimicrobial agents to combat airborne microbes and fungi.

In addition, the reflective coating can be included on any substrate, and may be utilized in any lighting device where a reflective coating or painting is present (e.g., fluorescent luminaires, reflectors inside of sealed lamps, cove enclosure surrounding light sources, architectural features that serve to reflect light, desk lamps, and other fixtures that distribute light from a light source.

Furthermore, the present teaching is not limited to medical settings. The present teaching is applicable in other industrial applications where the control of the growth of microbes and the reduction of microbial colonization are desired. In addition to a hospital setting, some of the other applications of the antimicrobial lighting fixture 100 include, for example, nursing homes, hotels, schools, food processing facilities, agricultural facilities, pools, medical devices production, pharmaceutical packaging, and research and development facilities.

Alternative embodiments, examples, and modifications which would still be encompassed by the disclosure may be made by those skilled in the art, particularly in light of the foregoing teachings. Further, it should be understood that the terminology used to describe the disclosure is intended to be in the nature of words of description rather than of limitation.

Those skilled in the art will also appreciate that various adaptations and modifications of the preferred and alternative embodiments described above can be configured without departing from the scope and spirit of the disclosure. Therefore, it is to be understood that, within the scope of the appended claims, the disclosure may be practiced other than as specifically described herein.

We claim:

1. A lighting system comprising:
  a lighting fixture comprising a light source, wherein the light source comprises at least one LED that emits a wavelength that contains ultraviolet wavelengths;
  a multilayer thin film coated reflector applied to an outer light emitting surface of the lighting fixture, wherein the multilayer thin film reflector comprises alternating layers of a first dielectric material having a relatively high refractive index and a second dielectric material having a relatively low refractive index; and
  a top layer of the multilayer thin film coated reflector comprises a material including an anatase $TiO_2$ crystal structure that exhibits antimicrobial properties when activated by the light source;
  wherein the top layer comprises an anatase $TiO_2$ crystal structure material doped with a doping material selected from at least one of silicon, zinc, iron, manganese, and combinations thereof.

2. The system according to claim 1, wherein the low refractive index material comprises a material that includes $SiO_2$ or a SiO hybrid material.

3. The system according to claim 1, wherein the high refractive index material comprises a material that includes $TiO_2$ or a TiO hybrid material.

4. The system according to claim 1, wherein the multilayer thin film coated reflector further comprises a metal substrate.

5. The system according to claim 1, wherein the multilayer thin film coated reflector comprises a reflective coating having over a 90% specular reflectance at a nominal incident angle.

6. The system according to claim 1, wherein the doping material changes the material including the anatase crystal structure through absorption and activation energy of longer wavelengths.

7. A method for producing a lighting system including (i) an aluminum (Al) substrate for mounting a light emitting diode (LED) on a portion thereof, the LED being configured for emitting light waves in the ultraviolet (UV) spectrum and (ii) a reflector assembly formed on another portion of the substrate, the method comprising:
  applying a multilayer thin film on an inner surface of the substrate including (i) alternating layers of a first dielectric material having a relatively high refractive index and (ii) a second dielectric material having a relatively low refractive index, the multilayer thin-film including predominantly silica ($SiO_2$) and titanium dioxide ($TiO_2$);
  applying an amorphous $TiO_2$ outer layer atop an exterior surface of the multilayer thin film; and
  applying an annealing process to the outer layer (i) at a temperature within a range of about 400°- 500° C. and (ii) in a controlled oxygen environment, the annealing converting the amorphous $TiO_2$ to an anatase $TiO_2$ crystal structure.

8. The method according to claim 7, further comprising energizing the LED to emit the UV light waves, the UV light waves activating a photocatalyst antimicrobial effect.

9. The method according to claim 7, wherein the annealing includes a rapid thermal annealing (RTA) process.

10. The method according to claim 7, wherein the anatase $TiO_2$ crystal structure is doped with a doping material selected from at least one of silicon, silver, zinc, iron, manganese, and combinations thereof.

11. The method according to claim 7, wherein the controlled oxygen environment includes an oxygen deficient $TiO_2$-channel.

* * * * *